US00PP17162P3

(12) United States Plant Patent

Clark et al.

(10) Patent No.: US PP17,162 P3

(45) Date of Patent: Oct. 24, 2006

(54) BLACKBERRY PLANT NAMED 'OUACHITA'

(50) Latin Name: ***Rubus* sp.**
Varietal Denomination: Ouachita

(75) Inventors: John Reuben Clark, Fayetteville, AR (US); James Norman Moore, Fayetteville, AR (US)

(73) Assignee: University of Arkansas division of Agriculture, Fayetteville, AR (US)

( * ) Notice: Subject to any disclaimer, the term of this patent is extended or adjusted under 35 U.S.C. 154(b) by 235 days.

(21) Appl. No.: 10/379,483

(22) Filed: Mar. 3, 2003

(65) Prior Publication Data

US 2004/0199968 P1 Oct. 7, 2004

(51) Int. Cl.
*A01H 5/00* (2006.01)

(52) U.S. Cl. ..... Plt./203

(58) Field of Classification Search ..... Plt./203
See application file for complete search history.

*Primary Examiner*—Anne Marie Grunberg
*Assistant Examiner*—Georgia Helmer

(57) ABSTRACT

Description and specifications of a new and distinct blackberry variety which originated from seed produced by a a hand pollinated cross of Navaho (U.S. Plant Pat. No. 6,679)×Arkansas selection 1506 (non-patented) is provided. This new blackberry variety can be distinguished by its high fruit yields, large fruit size, erect thornless canes, mid-season ripening, prolific fruiting row establishment, and good fruit quality.

3 Drawing Sheets

SUMMARY OF THE INVENTION

The new and distinct variety of blackberry originated from a hand pollinated cross of Navaho (U.S. Plant Pat. No. 6,679)×Arkansas selection 1506 (non-patented) made in 1990 at the Arkansas Agricultural Experiment Station Fruit Substation at Clarksville, Ark.

Plants and fruit of this new variety differ phenotypically from its parents. The new variety is earlier ripening, larger in fruit size and has more erect canes than the parent Navaho (U.S. Plant Pat. No. 6,679), and is more productive and erect-caned than the parent A-1506. The new variety retains larger fruit size throughout the harvest season than either of the parent blackberries. Although blackberries (*Rubus* sp.) are highly heterogeneous and outcrossing, and most clones contain genes from more than one species, the new variety and its progenitor lines phenotypically exhibit characters predominately of the erect eastern United States species, *Rubus allegheniensis* Porter (highbush blackberry) possibly introgressed with *R. argutus* Link. (tall blackberry). Its genes for thornlessness were derived frm the British cultivar Merton Thornless (non-patented), a derivative of *Rubus ulmifolius* Schott.

The seeds resulting from this controlled hybridization were germinated in a greenhouse in the spring of 1991 and planted in a field on the Arkansas Agricultural Experiment Station in Clarksville, Ark. The seedlings fruited during the summer of 1993 and one, designated Ark. 1905, was selected for its mid-season of ripening, large fruit size, excellent fruit quality, erect plant growth habit, and thornless.

During 1993, the original plant selection was propagated asexually from root cuttings, at the above noted location, and a test row of 20 plants was established. Subsequently, larger test plantings have been established with asexually multiplied plants at three locations in Arkansas. Additionally, the variety has been tested at state experiment stations in Griffin, Ga., Jackson, Ky., West Lafayette, Ind., Calhoun, La., Benton Harbor, Mich., and Aurora, Oreg., and at each location propagation was from root cuttings.

The new variety has been asexually multiplied annually since 1993 by the use of root cuttings and by rooting softwood cuttings. It forms new plants from adventitious buds on root cuttings more readily than its parent Navaho (U.S. Plant Pat. No. 6,679). During all asexual multiplication, the characteristics of the original plant have been maintained and no aberrant phenotypes have appeared.

Test plantings over a wide geographic area have shown this new variety to be adapted to differing soil and climatic conditions.

Plants of the new variety are vigorous and prolific and row establishment following planting is more rapid than with many other thornless varieties. Both primocanes and floricanes are erect in growth habit, and self-supporting, requiring no trellis support. The plants are genetically thornless, having the recessive genes for thornless derived from the variety Merton Thornless (non-patented). Plants and fruit are moderately tolerant to anthracnose [*Elsinoe veneta* (Burkh.) Jenkins], and plants appear immune to orange rust [*Gymnoconia nitens* (Schwein.) F. Kern and H. W. Thurston.] and double blossom/rosette [*Cercosporella rubi* (Wint.) Plakidas] The bloom period of the new variety averages 0 to 2 days earlier than the cultivar Navaho (U.S. Plant Pat. No. 6,679).

Fruit of the new variety begins ripening 7 days earlier than the Navaho (U.S. Plant Pat. No. 6,679) variety, and has a similar fruiting period to this variety of average 35 days. Average first ripening date is June 12 in central Arkansas. Fruit yields of the new variety are usually 5 to 7 lb/plant and are usually significantly higher than the Navaho (U.S. Plant Pat. No. 6,679) variety (with yields of 3 to 4 lb/plant) at all test locations and are comparable to the high yielding Apache (U.S. Plant Pat. No. 11,865) variety (5 to 7 lb/plant). Yields are consistent from year to year.

The fruit is conical in shape, bright glossy black in color and very attractive. The fruit is large (6–7 g) and 1.0 to 1.5 g larger than the size of the Navaho (U.S. Plant Pat. No. 6,679) variety. Fruit size of the new variety is maintained well throughout the entire harvest season. The new variety exhibits excellent fruit fertility with full drupelet set in contrast to Navaho (U.S. Plant Pat. No. 6,679), which has some drupelet sterility. The fruit is very firm at maturity, rating more firm than the Shawnee (U.S. Plant Pat. No. 5,686) and Choctaw (U.S. Plant Pat. No. 6,678) varieties, and nearly as firm as the Navaho (U.S. Plant Pat. No. 6,679) variety. Storage ability of fresh fruit of the new variety is superior to both the Shawnee (U.S. Plant Pat. No. 5,686) and Choctaw (U.S. Plant Pat. No. 6,678) varieties in that fruit firmness is superior to these varieties and resulting storage period is longer, and is comparable to the Navaho (U.S. Plant Pat. No. 6,679) variety.

The fresh fruit rates good in flavor, being comparable to Navaho (U.S. Plant Pat. No. 6,679) variety. The flavor is sweet and mildly subacid, with a distinct blackberry aroma. Flavor is sweeter and more aromatic than the Shawnee (U.S. Plant Pat. No. 5,686) variety. The soluble solids concentration averages 9.9%, but ranges up to 12%, which is higher than most other blackberry varieties, but slightly less than Navaho (U.S. Plant Pat. No. 6,679) (11.9% average). Dry seed weight averages 4.5 mg/seed, and seeds are comparable to those of the Navaho (U.S. Plant Pat. No. 6,679) and slightly smaller than those of Apache (U.S. Plant Pat. No. 11,865).

Fruit clusters are medium-large, cymose, and are mostly borne on the periphery of the plant canopy, providing easy access to harvest. Flower fertility is high and clusters are well filled.

The new variety has been named the Ouachita cultivar.

BRIEF DESCRIPTION OF THE PHOTOGRAPHS

The accompanying photographs show typical specimens of the individual fruit (FIG. 1), erect primocanes with floricanes beneath (FIG. 2), and individual primocane leaf (FIG. 3) of the new variety in color as nearly true as it is reasonably possible to make in a color illustration of this character.

DETAILED DESCRIPTION OF THE NEW VARIETY

The following is a detailed description of the botanical and pomological characteristics of the subject blackberry. Color data are presented in Royal Horticultural Society Colour Chart designations.

Where dimensions, sizes, colors and other characteristics are given, it is to be understood that such characteristics are approximations of averages set forth as accurately as practicable.

The descriptions reported herein are from specimens grown at Clarksville, Ark. unless otherwise noted.

Plant:

*Size.*—Medium, erect.

*Growth habit.*—Vigorous, with moderate suckering from crowns, moderate suckering from roots, canes erect.

*Growth rate.*—Primocanes reach tipping height (107 cm) in 51 days from emergence.

*Productivity.*—High and for duration of five weeks; consistent from year to year. Yields consistently range from 5 to 7 lb/plant, exceeding Navaho (U.S. Plant Pat. No. 6,679) (with yields of 3–4 lb/plant).

*Cold hardiness.*—Hardy to −17° C., slightly less than Navaho (U.S. Plant Pat. No. 6,679).

*Canes.*—Thornless, erect. Cane diameter: base 1.50 cm, midpoint 1.41 cm, terminal 1.19 cm. Internode length: base 5.52 cm, midpoint 5.62 cm, terminal 4.66 cm. Floricane (winter cane) color: base — Greyed Orange Group (166A); midpoint — Yellow Green Group (146A); terminus — Green Group (144A). Primocane color: base— Greyed — Purple Group (187A); midpoint — Greyed-Purple Group (187B); terminus — Greyed-Purple Group (183A). Date of primocane emergence: Julian 98.

*Disease resistance.*—Moderate to anthracnose; immune to orange rust and double blossom/rosette.

Foliage:

*Primocane.*—Leaves. — Large. Mature compound leaf width 22.20 cm; length 24.80 cm. Leaflet: Width 8.08 cm; length 16.26 cm; shape roundish to ovate with acuminate to acute apex and cordate base; margin serrated, serration teeth length 0.55 cm, and width at base 0.37 cm; moderately-heavy pubescence on abaxial and light pubescence on adaxial surfaces. Number of leaflets per compound leaf: 5. Color: Base abaxial — Green Group (137C); adaxial — Green Group (137A); midpoint abaxial — Green Group (137D); adaxial — Green Group (137A); terminal abaxial — Green Group (138A); adaxial — Green Group (137C). Petioles — Length: 8.29 cm. Color: Yellow Green Group (148A). Petiolules — Length: 3.48 cm. Color: Green Group (144A). Stipules — Length: 1.68 cm. Width: 0.16 cm.

*Floricane.*—Leaves — Large. Mature compound leaf width 14.45 cm; length 15.55 cm. Leaflet: width 4.65 cm; length 7.60 cm; shape ovate, with acute apex and sagittate base; margin serrated, with serration teeth length 0.43 cm and width at base 0.49 cm; moderate pubescence on abaxial and light pubescence on adaxial surfaces. Number of leaflets per compound leaf: 3. Color: base abaxial — Green Group (147B); adaxial — Green Group (139A); midpoint abaxial — Green Group (147B); adaxial — Green Group (139A); terminal abaxial — Green Group (147B); adaxial — Green Group (139A). Petioles — Length: 5.2 cm. Color: Yellow-Green Group (146B). Petiolules — Length 1.63 cm. Color: Yellow-Green Group (146B). Stipules — Length: 1.18 cm. Width: 0.27 cm.

Flowers:

*Date of bloom.*—First — Julian 117; 50% — Julian 125; Last — Julian 143.

*Blossom color.*—Red-Purple Group (62D).

*Reproductive organs.*—Stamens — erect, numerous. Pistils — numerous. Pollen — normal and abundant.

*Flower diameter.*—3.88 cm.

*Petal size.*—Length: 1.42 cm. Width: 1.14 cm.

*Number flowers per cluster.*—5 to 7.

*Number of petals per flower.*—5.

*Number of sepals per flower.*—5.

*Peduncle length.*—4.07 cm.

*Peduncle color.*—Yellow-Green Group (146C).

*Cyme type.*—Elongate simple cyme.

Fruit:

*Maturity.*—Mid-season, 7 days before Navaho (U.S. Plant Pat. No. 6,679). Average first ripe date is June 12. Average period of ripening is June 12 to July 17.

*Size.*—Large, average 6.0 g, uniform. Diameter: Fruit at primary position on inflorescence: equator 2.03 cm, base pole 1.74 cm, terminal pole 1.41 cm; fruit at secondary positions on inflorescence: equator 1.88 cm., base pole 1.69 cm, terminal pole 1.36 cm. Length (Primary fruit) 2.21 cm.

*Shape.*—Round oblong to conical, uniform.

*Color.*—Glossy black; Black Group (202A).

*Drupelet size.*—Medium, 0.56 cm.

*Seed size.*—Medium, 4.5 mg (dry wt., individual seed).

*Soluble solids.*—9.9%.

*pH.*—2.88 (as measured by pH meter on undiluted juice from a sample of 25 fully-ripe berries).

*Acidity.*—0.97 g tartaric acid/100 ml.

*Processed quality.*—Not evaluated in processing.

*Uses.*—Fresh is main use but can be processed for jellies, jams, juice, wine.

The variety: The most distinctive features of the variety are its high yields, large fruit size, mid-season fruit ripening, erect thornless canes, prolific fruiting row establishment, and good fruit quality.

We claim:

1. A new and distinct variety of blackberry plant, substantially as illustrated and described, characterized by its high yields, large fruit size, erect thornless canes, mid-season ripening, prolific fruiting row establishment, and good fruit quality.

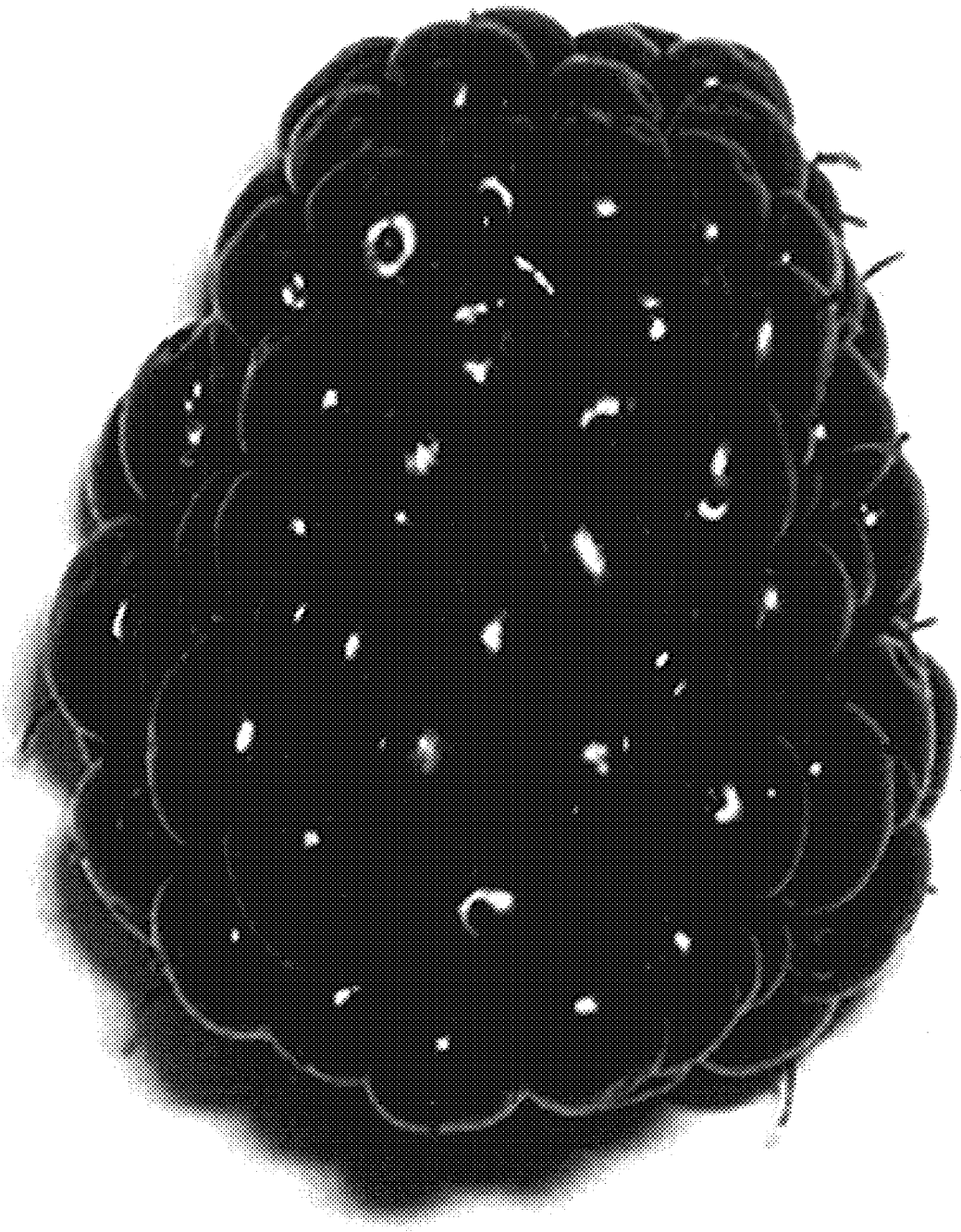

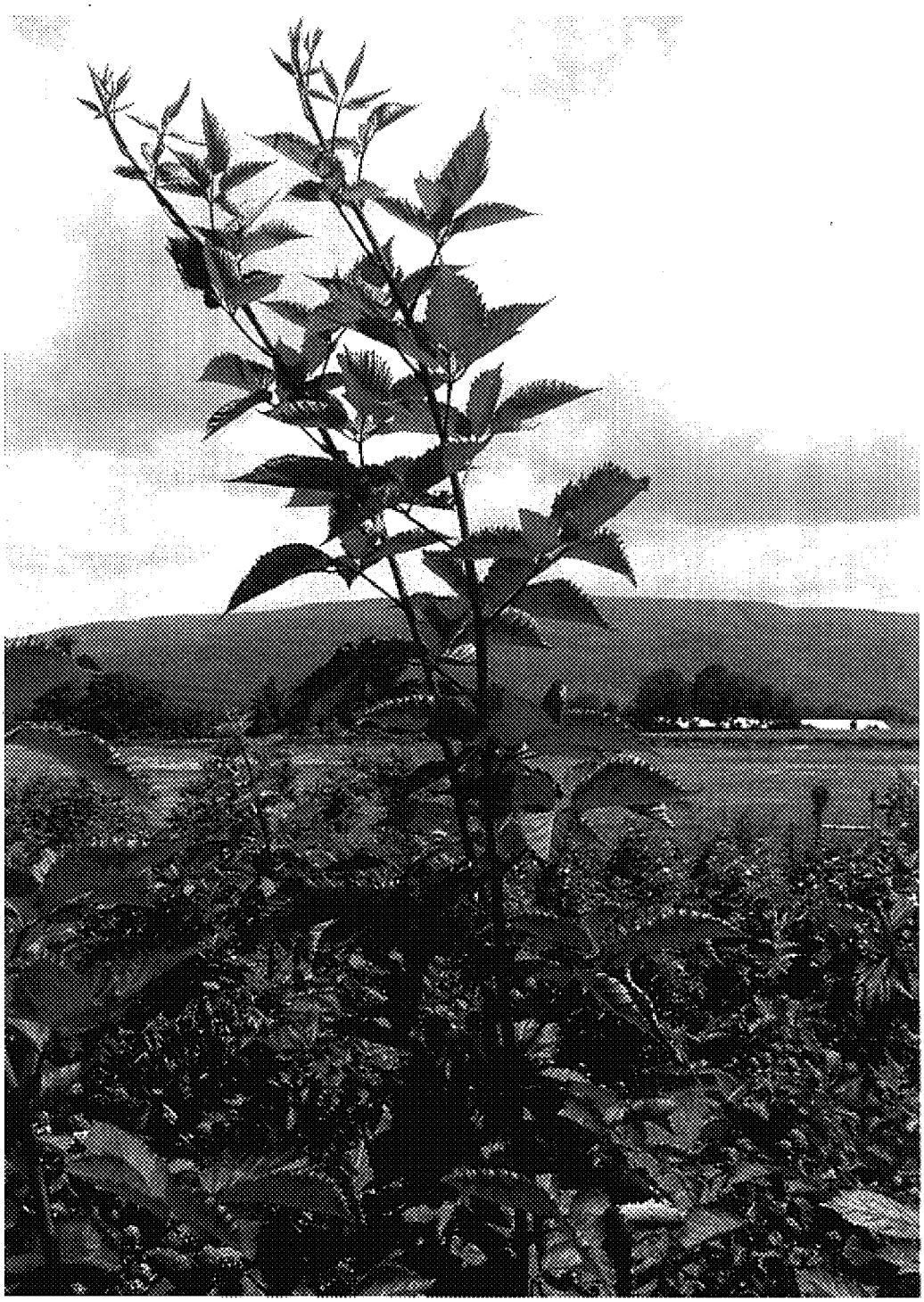

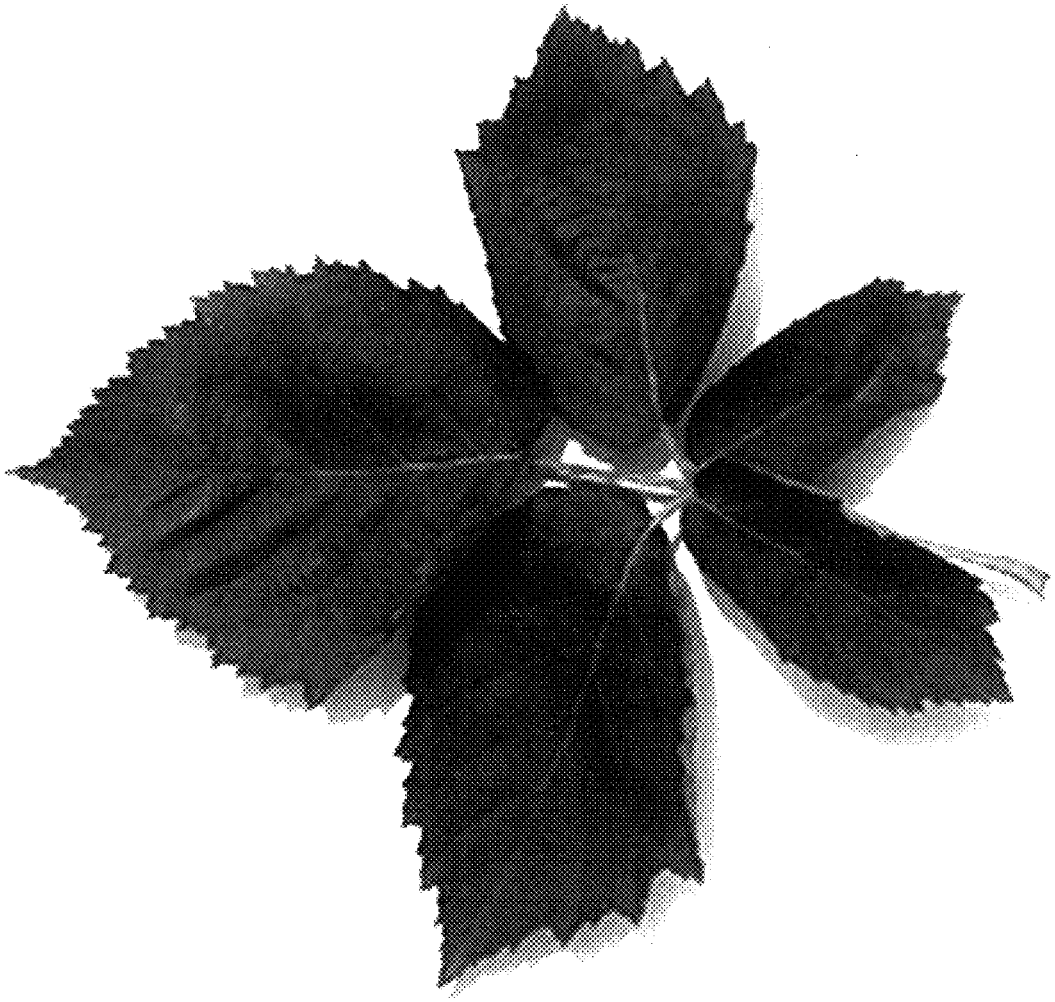

* * * * *